United States Patent [19]

Gschwendtner

[11] 4,435,609

[45] Mar. 6, 1984

[54] ISOMERIZATION OF BUTENE-1 TO BUTENE-2 IN ISOBUTYLENE

[75] Inventor: Wolfgang W. J. Gschwendtner, Cologne, Fed. Rep. of Germany

[73] Assignee: Exxon Research & Engineering Co., Florham Park, N.J.

[21] Appl. No.: 499,351

[22] Filed: May 31, 1983

[30] Foreign Application Priority Data

Jun. 8, 1982 [GB] United Kingdom ............... 8216535

[51] Int. Cl.$^3$ ........................... C07C 5/30; C07C 7/01
[52] U.S. Cl. .................................. 585/670; 585/664; 585/850; 585/855
[58] Field of Search ............... 585/664, 670, 850, 855, 585/671, 665, 666, 667, 668

[56] References Cited

U.S. PATENT DOCUMENTS

| | | | |
|---|---|---|---|
| 2,428,516 | 10/1947 | Drennen | 585/664 |
| 3,531,545 | 9/1970 | Garner et al. | 585/668 |
| 3,758,604 | 9/1973 | Sprecher et al. | 585/668 |
| 4,132,745 | 1/1979 | Amignes et al. | 585/668 |

FOREIGN PATENT DOCUMENTS

| | | | |
|---|---|---|---|
| 1002394 | 8/1965 | United Kingdom | 585/668 |
| 1003230 | 9/1965 | United Kingdom | 585/668 |
| 1110826 | 9/1966 | United Kingdom | 585/668 |
| 1350285 | 4/1972 | United Kingdom | 585/666 |
| 1455482 | 2/1974 | United Kingdom | 585/666 |
| 1595526 | 3/1978 | United Kingdom | 585/666 |

*Primary Examiner*—Delbert E. Gantz
*Assistant Examiner*—A. Pal
*Attorney, Agent, or Firm*—Rebecca Yablonsky

[57] ABSTRACT

Isobutylene containing a minor amount, e.g. 0.06–0.10 wt %, of n-butene-1 is subjected to gas phase isomerization using hydrogen and Group VIII metal catalyst to convert the butene-1 to butene-2 with at least 65% conversion and no more than 0.3% hydrogenation of the isobutylene; butene-2 is more readily separated from the isobutylene by distillation. Isomerization conditions applied are defined by a pressure of 3 to 5 bars gauge, a temperature of from 40° to 50° C., a space velocity of from 150 to 300 vol/vol/hour, a mass velocity of from 1.1 to 1.5 metric tons/m2/hour and a hydrogen/feed volume ratio of not more than 2.5%.

13 Claims, No Drawings

ISOMERIZATION OF BUTENE-1 TO BUTENE-2 IN ISOBUTYLENE

This invention relates to a method of converting butene-1 to butene-2 in a mixture comprising butene-1, butene-2 and isobutylene. Particularly but not exclusively the invention is concerned with such a method which will reduce the butene-1 content of a contaminated, albeit substantially pure isobutylene, to a level such that removal of butene-2 from the mixture by distillation leaves an isobutylene feed which is sufficiently pure for use in the efficient production of butyl rubber, and which is not substantially commercially devalued by a greatly increased isobutane content.

Isobutylene which is conventionally used in the production of butyl rubber is generally obtained from $C_4$ hydrocarbon mixtures, for example $C_4$ steam cracked naphtha or gas oil cuts. Such mixtures usually contain (in addition to the desired isobutylene), normal butenes, acetylenes and butadiene. Conventionally a relatively pure isobutylene stream is produced by hydrofining the mixture to remove the acetylenes and dienes, and then carrying out an acid extraction procedure. In this the crude product is reacted with sulphuric acid to yield a mixture of crude tertiary butyl alcohol (TBA) and normal butenes, from which the crude TBA may readily be separated to give a substantially hydrocarbon-free mixture of TBA and acid.

Passage of this product through a steam regenerator then yields a mixture of sulphuric acid and impure isobutylene, which may readily be separated. The impure isobutylene thus produced contains small amounts of TBA, SBA (sec. butyl alcohol), butene-1, butene-2 and $C_4$ dimers and trimers. The TBA and SBA are removed by condensation and washing, so leaving an "impure" isobutylene contaminated with a minor amount of butene-1 and some butene-2. Removal of butene-1 from isobutylene by distillation is almost impossible since the two compounds have boiling points within 0.3 degrees C., and so it is usual to convert the butene-1 to butene-2 which is much more readily separable from the isobutylene. Thus, the normal boiling point of butene-1 is about $-6.7°$ C. and the normal boiling point of isobutylene is about $-6.8°$ C., whereas the normal boiling points of cis- and trans-butene-2 are about $3.7°$ C. and $0.9°$ C. respectively.

There is a commercial advantage in being able to reduce the butene-1 content of a slightly impure or contaminated isobutylene feed from the relatively minor amounts of, say, 0.05-0.5 wt%, particularly 0.06-0.10 wt% which are attainable by known techniques such as acid extraction and catalytic purification, to much lower (minimal) values which will not substantially hinder further processing of the isobutylene. Typically the product of the above mentioned acid extraction method of "purification" contains up to 0.3 wt% butene-1, and there is a need for further reduction of this content to permit efficient further processing. At the same time it is desirable to restrict production of butanes, particularly isobutane, which would serve to devalue the product.

The purification of crude $C_4$ cut feedstock to reduce the content of butene-1 has formed the subject matter of several published papers and patents. However the majority of these are concerned with the reduction of butene-1 content in the feed to the sort of minor amounts which are the starting point contents of the merely "contaminated" feeds treated according to the instant invention. Moreover the specific combination of parameters and catalyst which has been found so effective for minimising butene-1 content according to the invention are nowhere disclosed or taught.

According to Eleazar et al (Hydrocarbon Processing, May 1979, pp 112–118), butene streams for petrochemical or motor gas alkylation use may be upgraded by simultaneous hydrogenation (to reduce butadiene content) and isomerisation (butene-1 to butene-2). The method disclosed uses a precious metal catalyst and hydrogen in conjunction with a liquid phase fixed bed reactor configuration. The importance of space velocity, temperature and pressure are recognised, but the method is restricted to liquid phase operation and uses feeds containing major amounts of butene-1.

U.S. Pat. No. 4,260,840 (Exxon) relates to purification of $C_4$ streams, but here the requirement is to selectively hydrogenate butadiene in streams which contain at least 30% butene-1, without isomerization of butene-1 to butene-2 and without hydrogenation of butenes to butane. The object of the invention is here achieved using hydrogen and a palladium catalyst, but under high temperature and pressure conditions sufficient to maintain the hydrocarbons in a mixed vapour-liquid phase.

GB No. 1,455,493 (UOP) relates to isomerisation of butene-1 to butene-2 and discloses a catalyst for achieving such isomerisation in the presence of isobutylene. The catalyst used is sulphided nickel on a carrier, and is prepared by forming elemental nickel or nickel oxide on the carrier, sulphiding, and stripping the sulphided catalyst with hydrogen to reduce the sulphur content to a defined amount. Isomerisation using such catalyst and hydrogen is preferably performed in the gas phase, preferably at high temperatures of 75° to 160° C. and is performed on feeds which contain relatively large proportions of butene-1. Specifically exemplified are feeds which contain 55 to 60 mole % propane, the remainder being olefin in 2:1 butene-1 to isobutylene volume ratio e.g. 65–68 mole % butene-1:32–35 mole % isobutylene. Comparison examples using elemental nickel as catalyst are said to show that at temperatures of 110°, 130° and 140° C. such catalysts are unstable and low in activity. There is no suggestion that such elemental catalyst can serve to convert minor amounts of butene-1 to minimal amounts in a "contaminated" isobutylene feed under certain specifically defined vapour phase conditions.

GB No. 1,110,826 (BP) teaches the isomerisation of butene-1 to butene-2 in the presence of isobutylene and optionally hydrogen using a catalyst comprising elemental nickel which is carried on a support and partially sulphided to a defined extent. The conversion may be performed under liquid, vapour or mixed phase conditions over a wide range of temperatures (0°–300° C., preferably 50°–150° C.) and pressures. Apart from using a different catalyst system compared with the instant invention, and less well defined process conditions, this patent is not concerned with the conversion of low amounts of butene-1 in already substantially pure isobutylene feed to minimal amounts. Thus in the example the feed contains 22.5 wt% butene-1 (based on total) or 26.3 wt% based on total butenes content, with the isomerisation method reducing these values to 4.0 wt% and 4.5 wt% respectively.

U.S. Pat. No. 3,758,604 (Esso) teaches a multistage isomerisation-fractionation process from removing isobutylene from mixtures which also contain butene-1, with the aim of obtaining isobutylene with butene-1 levels of lower than 3% down to 0.1% or even lower. A first isomerisation stage converts the mixture to isobutylene containing at most 3 wt% n-C$_4$ olefins and, following fractionation, a second isomerisation stage reduces the butene-1 content to less than 1 wt%. Isomerisation is performed at relatively low temperatures (−50° to +100° C.) in either the vapour or liquid phase. The catalysts exemplified are cobalt II acetylacetonate supported on silica and reduced by triisobutyl aluminium, and sodium on alumina; in the second stage isomerisation, where the lowest butene-1 content feed is employed (as product of the fractionation following the first isomerisation stage), a temperature of 38° C. is used to yield a product containing 0.064 wt% butene-1, based on total C$_4$s (0.09 wt% based on isobutylene content). The product of this process therefore corresponds to the "contaminated" starting feed stream for the instant invention; moreover there is no suggestion to employ hydrogen in the isomerisation process.

GB No. 1,595,526 (UOP) teaches the separation of iso olefins and an olefins from a mixture thereof, particularly isobutylene and n-butene, by fractionation to give an isobutylene rich stream containing 1-butene which is then isomerised to convert the 1-butene content, this isomerised stream being in part returned as reflux to the fractionation stage and in part removed as "purified" isobutylene. A nickel subsulphide is used as catalyst, optionally with hydrogen present in the stream and an assessment of the example shows that this patent is concerned with forming as its end product the contaminated, albeit substantially pure isobutylene streams which are nevertheless the "crude" starting materials for the instant invention. Thus the exemplified product contains 0.74% butene-1 based on total C$_4$ olefin and 0.80% butene-1 based on isobutylene.

GB No. 1,350,285 (BP) teaches the removal of butene-1 from hydrocarbon feeds using a noble metal catalyst. Isomerisation is said to occur in the presence of hydrogen in the liquid or vapour phase, but at an extremely low temperature of 0° to −70° C. Assessment of the examples again shows that the product stream of this prior art patent has a butene-1 content which corresponds with the starting feed of the instant invention.

According to the present invention there is provided a method of treating an isobutylene feed which contains undesired minor amounts of n-butene-1 to convert said undesired minor amounts of n-butene-1 to n-butene-2 with at least 65% conversion and no more than 0.3% hydrogenation, which method comprises passing the isobutylene feed and hydrogen, in the gas phase, over a catalyst comprising a Group VIII metal under isomerisation conditions defined by a pressure of from 3 to 5 bar gauge, a temperature of from 40° to 50° C., a space velocity of from 150 to 300 vol/vol/hr at operating temperature and pressure, a mass velocity of from 1.1 to 1.5 metric tons/m$^2$/hour and a hydrogen/isobutylene feed volume ratio of not more than 2.5% at operating temperature and pressure.

As mentioned hereinbefore, the isobutylene feed may contain for example 0.05 to 0.5 wt%, say up to 0.3 wt%, particularly from 0.06 to 0.10 wt%, e.g. about 0.15 wt% of n-butene-1. Preferably the feed contains in excess of 98 or 99 wt% isobutylene based on C$_4$ content. This may be the product obtained following acid extraction or direct liquid phase hydroisomerisation of a crude C$_4$ cut feed stock. It has been found that by using the method of the invention it is possible to reduce the minor amounts of butene-1 in such feedstock to minimal amounts of about 0.01%-0.02 wt%.

According to the invention the isomerisation is performed in the vapour phase, in contrast to some other known methods; otherwise, catalyst failure has been detected. The pressure at which the conversion takes place, i.e. from 3 to 5 bar gauge, preferably from 3.5 to 4.5 bar gauge and more preferably about 4 bar gauge, has been found, when used in conjunction with the other defined parameters of the method, to yield good (at least 65%, and typically 75–85%) conversion to mainly trans-butene-2 with low (no more than 0.3%, and typically 0.08–0.15%) hydrogenation.

Outside the range only a poor conversion generally is obtained, and there may also be undesirably high hydrogenation of the isobutylene to isobutane, which greatly devalues the feed.

Temperatures within the specified range, preferably 42°–48° C. and more preferably about 45° C., again when used in conjunction with the other defined parameters, have been found generally to give conversions of 65% or more, which are commercially acceptable for further processing of the feed. Temperatures in excess of this range, say 55° C., have been found to give in the region of only 60% conversion and somewhat high hydrogenation, which is not commercially acceptable. This is in contrast with the known liquid phase conversion which is operated at temperatures of about 80° C., it being believed that lower temperatures lead to shorter catalyst life in that particular process.

The space velocity parameter of the method is the volume per hour of the feed stream, at the operating temperature and pressure, per unit volume of the catalyst. Within the specified range, a preferred range of 200–260, and particularly a value of about 240 has been found to give good results within the scope of the invention.

The mass velocity of the system is from 1.1 to 1.5 defined in units of metric tons per square meter cross sectional area of the reactor tube per hour. A preferred operating range for the system is 1.2–1.4, particularly about 1.3.

A limited hydrogen supply is required as catalyst promoter in order to obtain good conversion of butene-1 to butene-2. However, it is important that excess hydrogen is not present since this would lead to hydrogenation of the isobutylene to isobutane. According to the invention the maximum hydrogen/isobutylene feed rate is 2.5% volume, that is a maximum ratio of hydrogen volume to contaminated isobutylene feed volume, at the conditions of isomerisation, of 0.0250:1. Preferably the ratio is in the range 0.5–1.5 vol %. Under these conditions it has proved possible to restrict the isobutylene hydrogenation to 0.3% or less, as compared with values of 3% which are typically found with relatively high temperature and high pressure processes.

The catalyst system used in accordance with the invention comprises a metal of Group VIII of the periodic classification of the elements, preferably palladium or rhodium. In a preferred embodiment the catalyst system comprises the metallic catalyst supported on an inert support such as alumina. The catalyst system may contain from 0.005 to 1.0 wt% of the group VIII metal on the support, preferably from about 0.01 to 0.1 wt%.

In a particularly preferred embodiment the catalyst system contains a Group VIa metal such as chromium, in addition to the Group VIII metal. The periodic classification referred to above may be found for example in "Advanced Inorganic Chemistry", Cotton and Wilkinson, 2nd Edition (1966), Interscience.

A commercially available catalyst which has been found to be suitable for use in accordance with the invention is catalyst G55B manufactured by the Girdler Corporation, Louisville, Ky., USA. This is a palladium on alumina catalyst in the form of spheres of 3×6 mesh. The chemical composition in wt% is Pd=0.03, Cr=0.03, $Al_2O_3$=99.7 with minor amounts of Fe and Ni. Physical properties of this catalyst according to the manufacturer's data sheet are: bulk density=45 + or −3 lbs/cuft, surface area=150–200 $m^2/g$, pore volume=0.35–0.45 cc/g.

Another commercially available catalyst suitable for use in the method is the Houdry catalyst H1424-005, a palladium on alumina catalyst in the form of 4×6 mm extrudates having the chemical composition (wt%) of Pd=0.05, $Al_2O_3$=96.0 $Na_2O$=0.4, with other minor components. Physical properties of this catatalyst are bulk density=0.8 g/cc, surface area=80 $m^2/g$, pore volume=0.5 cc/g.

In a particularly preferred embodiment, the method comprises passing isobutylene containing 0.06 to 0.10% butene-1, and hydrogen, in the gas phase, over a catalyst comprising palladium or palladium/chromium on alumina under isomerisation conditions defined by a pressure of 3.5 to 4.5, preferably about 4 bar gauge, a temperature of 42° to 48° C., preferably about 45° C., a space velocity of 200–260, preferably about 240 vol/vol/hr, a mass velocity of 1.2–1.4, preferably about 1.3 metric tons/$m^2$/hour and a hydrogen/feed ratio of not more than 2.50% volume preferably 0.5 to 1.5 vol%, to convert at least 65%, preferably 75–85% of the butene-1 to butene-2 with no more than 0.3%, preferably 0.08–0.15% hydrogenation of isobutylene to isobutane.

By using the above mentioned catalysts in the embodiment, it has proved possible to carry out the conversion required, the conversion extremes hitherto obtained being an 83% conversion of butene-1 to mainly trans-butene-2, with 0.15% hydrogenation of isobutylene using the Girdler catalyst, and 67% conversion with 0.08% hydrogenation using the Houdry catalyst.

The invention is illustrated by the following Examples of which nos. 1 to 3 and 7 to 13 are included by way of comparison. The operating conditions adopted for each Example, and the analytical results for the product, are listed in the Table. In each case the feed which was subjected to treatment under the tabulated conditions was a commercially available isobutylene feedstock having the following composition in % by weight:

isobutylene=99.79
isobutane=0.004
n-butene-1=0.061
trans n-butene-2=0.072

The catalyst which was used for Examples 1 to 8, without noticeable deterioration, was Girdler catalyst G55B, being principally palladium and chromium on alumina as defined hereinbefore. That which was used for Examples 9 to 15 was the palladium on alumina Houdry catalyst H 1424-005 as defined hereinbefore.

As may be deduced from the tabluated data, Comparison Examples 1, 2 and 3 show that a high hydrogen/feed ratio gives a hydrogenation level which is not commercially desirable and which increases with operating temperature, even though the conversion is good. The combination of high hydrogen/feed ratio, high space velocity and high mass velocity (Comparison Examples 7 and 8) gives very poor conversions, and a low hydrogenation which is believed to reflect that high throughput enables little reaction to take place. On the other hand, Examples 4, 5 and 6 show that by maintaining the isomerisation conditions according to the invention it is possible to obtain a good conversion of butene-1 to butene-2, with acceptably low hydrogenation to isobutane.

Comparison Examples 9 and 10 show the effect of space velocity on the product. Thus high space velocity results in a much poorer conversion to butene-2. In both Examples there is a high hydrogen flow rate, and hence hydrogenation takes place to an unacceptably high level in excess of 1%. Comparison Examples 11, 12 and 13 show that reduction of the space velocity to within the range required in accordance with the invention gives a generally improved % conversion. However, maintenance of a relatively high hydrogen feed rate produces hydrogenation which is greater than the desired maximum value of 0.3%. Examples 14 and 15 show that by maintaining the isomerization conditions in accordance with the invention a product which is acceptable in terms of both conversion and hydrogenation is obtained.

Numerous other runs not described herein have shown that the particular combination of parameter ranges specified is required to give acceptable results. By this it is meant that the isobutylene feed has had a minor butene-1 content reduced to a minimal level such that it does not substantially interfere with further processing of the feed, particularly for butyl rubber production, and that hydrogenation is sufficiently low that there is minimal downgrading of the feed.

TABLE

| Example | H₂ (vol %) | P(bar gauge) | T(°C.) | Space Velocity (v/v/hr) | Mass Velocity (tonne/m²/hr) | Isobutane | 1-butene | isobutene | 2-butene | Conversion (%) |
|---|---|---|---|---|---|---|---|---|---|---|
| 1 | 5.0 | 4.0 | 40 | 235 | 1.3 | 0.89 | 0.007 | 99.0 | 0.111 | 88.5 |
| 2 | 5.0 | 4.0 | 45 | 235 | 1.3 | 1.02 | 0.006 | 98.85 | 0.111 | 90.15 |
| 3 | 5.0 | 4.0 | 50 | 235 | 1.3 | 1.14 | 0.007 | 98.76 | 0.118 | 88.5 |
| 4 | 2.5 | 4.0 | 45 | 235 | 1.3 | 0.27 | 0.0105 | 99.55 | 0.115 | 82.8 |
| 5 | 1.25 | 4.0 | 45 | 235 | 1.3 | 0.15 | 0.010 | 99.72 | 0.115 | 82.8 |
| 6 | 2.5 | 4.0 | 45 | 168 | 1.3 | 0.25 | 0.015 | 99.62 | 0.106 | 75.4 |
| 7 | 12.5 | 4.0 | 88 | 1200 | 5.8 | 0.07 | — | — | — | 40 |
| 8 | 12.5 | 4.0 | 88 | 1100 | 5.5 | 0.07 | — | — | — | 21 |
| 9 | 10.0 | 4.0 | 50 | 1333 | 1.3 | 1.42 | 0.02 | 98.43 | 0.106 | 67.2 |
| 10 | 10.0 | 4.0 | 50 | 235 | 1.3 | 1.08 | 0.011 | 98.80 | 0.105 | 81.9 |
| 11 | 5.0 | 4.0 | 50 | 235 | 1.3 | 0.78 | 0.0106 | 99.09 | 0.111 | 82.6 |
| 12 | 5.0 | 4.0 | 45 | 235 | 1.3 | 0.65 | 0.009 | 99.23 | 0.113 | 85.2 |
| 13 | 5.0 | 4.0 | 40 | 235 | 1.3 | 0.33 | 0.011 | 99.54 | 0.116 | 81.9 |
| 14 | 2.5 | 4.0 | 40 | 235 | 1.3 | 0.083 | 0.0215 | 99.78 | 0.109 | 67.0 |

TABLE-continued

| Example | H₂ (vol %) | P(bar gauge) | T(°C.) | Space Velocity (v/v/hr) | Mass Velocity (tonne/m²/hr) | Product Composition (wt %) | | | | Conversion (%) |
| --- | --- | --- | --- | --- | --- | --- | --- | --- | --- | --- |
| | | | | | | Isobutane | 1-butene | isobutene | 2-butene | |
| 15 | 2.5 | 4.0 | 45 | 235 | 1.3 | 0.19 | 0.014 | 99.68 | 0.113 | 77.0 |

I claim:

1. A method of treating an isobutylene feed which contains 0.05 to 0.5 wt% of n-butene-1 to convert n-butene-1 to n-butene-2 with at least 65% conversion and at most 0.3% hydrogenation, which method comprises passing the isobutylene feed and hydrogen, in the gas phase, over a catalyst system comprising a Group VIII metal, under isomerisation conditions defined by a pressure of from 3 to 5 bar gauge, a temperature of from 40° to 50° C., a space velocity of from 150 to 300 vol/vol/hr at operating temperature and pressure, a mass velocity of from 1.1 to 1.5 metric tons/m²/hour and a hydrogen-/isobutylene feed volume ratio of at most 2.5% at operating temperature and pressure.

2. A method according to claim 1 wherein the isobutylene feed is the product of an acid extraction process carried out on a C₄ hydrocarbon cut.

3. A method according to claim 1, wherein the undesired amount of n-butene-1 comprises from 0.06 to 0.10 wt% of the feed.

4. A method according to claim 1, wherein the Group VIII catalyst metal is selected from palladium and rhodium.

5. A method according to claim 1 wherein the catalyst system additionally includes a Group VI A metal.

6. A method according to claim 1 wherein the catalyst system comprises the metal carried on an inert support.

7. A method according to claim 6 wherein the inert support is alumina.

8. A method according to claim 6 wherein the catalyst system contains from 0.005 to 1.0 wt% of Group VIII metal based on the weight of support.

9. A method according to claim 8 wherein the catalyst system contains from 0.01 to 0.10 wt% of Group VIII metal based on the weight of support.

10. A method of treating a normal butene-containing isobutylene feed to convert undesired amounts of n-butene-1 to n-butene-2 with at least 65% conversion and at most 0.3% hydrogenation, which method comprises passing the isobutylene feed and hydrogen, in the gas phase, over a catalyst system selected from palladium and palladium/chromium on alumina under isomerisation conditions defined by a pressure of from 3.5 to 4.5 bar gauge, a temperature of from 42° to 48° C., a space velocity of from 200 to 260 vol/vol/hr at operating temperature and pressure, a mass velocity of from 1.2 to 1.4 metric tons/m²/hour and a hydrogen/isobutylene feed volume ratio of at most 2.5% at operating temperature and pressure.

11. A method according to claim 10 wherein the operating pressure is about 4 bar gauge, the operating temperature is about 45° C., the operating space velocity is about 240 vol/vol/hr, and the mass velocity is about 1.3 metric tons/m²/hour.

12. A method according to claim 1 wherein the treated feed contains a minimal amount of from 0.01 to 0.02 wt% of n-butene-1.

13. A method according to claim 1 which includes the additional step of distilling the product mixture to remove n-butene-2 therefrom.

* * * * *